US008613712B1

(12) United States Patent
Burkett et al.

(10) Patent No.: US 8,613,712 B1

(45) Date of Patent: Dec. 24, 2013

(54) TEXTURED POLYMER COATED GUIDE WIRE AND METHOD OF MANUFACTURE

(75) Inventors: David H. Burkett, Temecula, CA (US); Kevin Britton, Murrieta, CA (US); Ryan Grandfield, Murrieta, CA (US); Peter J. D'Aquanni, Murrieta, CA (US); David Wrolstad, Temecula, CA (US); Edwin P. Mahieu, Temecula, CA (US); Wayne E. Cornish, Fallbrook, CA (US); Mark T. Richardson, Escondido, CA (US)

(73) Assignee: Abbott Cardiovascular Systems Inc., Santa Clara, CA (US)

(*) Notice: Subject to any disclaimer, the term of this patent is extended or adjusted under 35 U.S.C. 154(b) by 2422 days.

(21) Appl. No.: 10/664,004

(22) Filed: Sep. 16, 2003

(51) Int. Cl.
*A61B 5/00* (2006.01)

(52) U.S. Cl.
USPC .......... 600/585

(58) Field of Classification Search
USPC .......... 604/103.08, 164.13, 264, 523, 528; 600/434, 585
See application file for complete search history.

(56) References Cited

U.S. PATENT DOCUMENTS 4,538,622 A 9/1985 Samson et al.
4,748,986 A 6/1988 Morrison et al.
5,061,273 A 10/1991 Yock et al.
5,107,852 A 4/1992 Davidson et al.
5,135,503 A 8/1992 Abrams
5,228,453 A * 7/1993 Sepetka .......... 600/585
5,341,818 A 8/1994 Abrams et al.
5,345,945 A 9/1994 Hodgson et al.
5,404,887 A * 4/1995 Prather .......... 600/585
5,443,907 A * 8/1995 Slaikeu et al. .......... 428/375
5,498,250 A 3/1996 Prather
5,516,336 A 5/1996 McInnes et al.
5,606,979 A 3/1997 Hodgson
6,033,720 A * 3/2000 Stoltze et al. .......... 427/2.3
6,106,485 A 8/2000 McMahon
6,251,085 B1 6/2001 Tezuka
6,296,616 B1 * 10/2001 McMahon .......... 600/585
6,419,745 B1 7/2002 Burkett et al.
6,432,066 B1 8/2002 Ferrera
6,440,088 B1 8/2002 Jacobsen et al.
6,554,942 B2 4/2003 Solar et al.
6,638,266 B2 10/2003 Wilson et al.
2004/0010189 A1 * 1/2004 van Sloun et al. .......... 600/374
2004/0039309 A1 * 2/2004 Murayama et al. .......... 600/585

FOREIGN PATENT DOCUMENTS

WO WO 9925413 A1 * 5/1999
WO WO 01/36034 A2 * 5/2001

OTHER PUBLICATIONS

U.S. Appl. No. 10/608,788, Grandfield et al. *Coil Textured Heat Shrink Polymer Guide Wire*, filed Jun. 26, 2003.

* cited by examiner

*Primary Examiner* — Emily Schmidt
(74) *Attorney, Agent, or Firm* — Fulwider Patton LLP

(57) ABSTRACT

A guide wire for advancing a medical device such as a catheter through a patient's body lumen which has an elongated core with proximal and distal core section, a flexible tubular member such as a coil on the distal end. The wire core includes surface textures that are translated into the overlying coating. Alternatively, the coating has its own surface texture. The surface textures include randomly or non-randomly spaced bumps, divots, ridges, helical grooves, longitudinal grooves, undulations, etc.

5 Claims, 3 Drawing Sheets

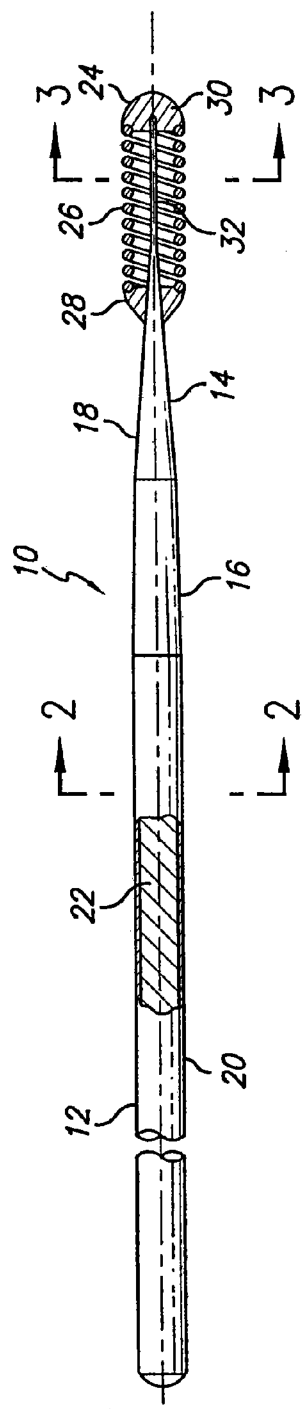
FIG. 1
26
32
FIG. 3
20
22
FIG. 2
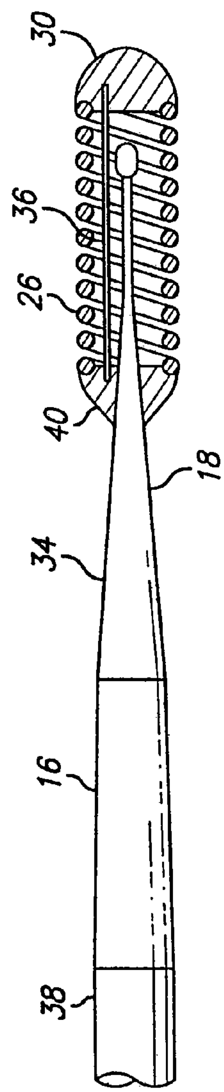
FIG. 4

TEXTURED POLYMER COATED GUIDE WIRE AND METHOD OF MANUFACTURE

BACKGROUND OF THE INVENTION

This present invention relates to the field of guide wires used for advancing intravascular devices such as stent delivery catheters, balloon dilatation catheters, and atherectomy catheters within a body lumen. More specifically, the present invention relates to a guide wire with a polymer coating having a textured surface.

Conventional guide wires for angioplasty, stent delivery, atherectomy and other vascular procedures usually comprise an elongated core with one or more tapered sections near the distal end thereof and a flexible body such as a helical coil or a tubular body of polymeric material disposed about the distal portion of the elongated core. A shapable member, which may be the distal extremity of the elongated core or a separate shaping ribbon which is secured to the distal extremity of the elongated core, extends through the flexible body and is secured to the distal end of the flexible body by soldering, brazing, or welding, which forms a rounded distal tip. Torquing means are provided on the proximal end of the elongated core to rotate, and thereby steer, the guide wire while it is being advanced through a patient's vascular system.

Further details of guide wires and devices associated therewith for various interventional procedures can be found in, for example, U.S. Pat. Nos. 4,748,986 (Morrison et al.); 4,538,622 (Samson et al.); 5,135,503 (Abrams), 5,341,818 (Abrams et al.), and 5,345,945 (Hodgson et al.), which are hereby incorporated herein in their entirety by reference thereto.

In a typical coronary procedure using a guide wire, a guiding catheter having a preformed distal tip is percutaneously introduced into a patient's peripheral artery, e.g., femoral or brachial artery, by means of a conventional Seldinger technique and advanced and steered therein until the distal tip of the guiding catheter is seated in the ostium of a desired coronary artery.

There are two basic techniques for advancing a guide wire into the desired location within the patient's coronary anatomy through the in-place guiding catheter. The first is a preload technique which is used primarily for over-the-wire (OTW) devices, and the second is the bare wire technique which is used primarily for rail type systems.

With the preload technique, a guide wire is positioned within an inner lumen of an OTW device such as a dilatation catheter or stent delivery catheter with the distal tip of the guide wire just proximal to the distal tip of the catheter and then both are advanced through the guiding catheter to the distal end thereof. The guide wire is first advanced out of the distal end of the guiding catheter into the patient's coronary vasculature until the distal end of the guide wire crosses the arterial location where the interventional procedure is to be performed, e.g., a lesion to be dilated or a dilated region where a stent is to be deployed. The catheter, which is slidably mounted onto the guide wire, is advanced out of the guiding catheter into the patient's coronary anatomy over the previously introduced guide wire until the operative portion of the intravascular device, e.g., the balloon of a dilatation or a stent delivery catheter, is properly positioned across the arterial location. Once the catheter is in position with the operative means located within the desired arterial location, the interventional procedure is performed. The catheter can then be removed from the patient over the guide wire. Usually, the guide wire is left in place for a period of time after the procedure is completed to ensure reaccess to the arterial location if it is necessary. For example, in the event of arterial blockage due to dissected lining collapse, a rapid exchange type perfusion balloon catheter such as described and claimed in U.S. Pat. No. 5,516,336 (McInnes et al.), can be advanced over the in-place guide wire so that the balloon can be inflated to open up the arterial passageway and allow blood to perfuse through the distal section of the catheter to a distal location until the dissection is reattached to the arterial wall by natural healing.

With the bare wire technique, the guide wire is first advanced by itself through the guiding catheter until the distal tip of the guide wire extends beyond the arterial location where the procedure is to be performed. Then a rail type catheter, such as described in U.S. Pat. No. 5,061,273 (Yock) and the previously discussed McInnes et al., which are incorporated herein by reference, is mounted onto the proximal portion of the guide wire which extends out of the proximal end of the guiding catheter outside of the patient. The catheter is advanced over the catheter, while the position of the guide wire is fixed until the operative means on the rail type catheter is disposed within the arterial location where the procedure is to be performed. After the procedure, the intravascular device may be withdrawn from the patient over the guide wire or the guide wire advanced farther within the coronary anatomy for an additional procedure.

There has been an interest in creating different surface profiles for the guide wire core. The interest arose primarily to address the issue of friction between the contact surface of the guide wire and the catheter lumen through which it passes or the body lumen of the patient. One attempt is the use of a sleeve at the distal portion of the core as seen in, for example, U.S. Pat. No. 5,404,887 (Prather). Another approach to reducing the surface contact between the guide wire and a catheter lumen or body lumen is shown in U.S. Pat. No. 6,296,616 (McMahon).

SUMMARY OF THE INVENTION

The present invention in various embodiments is directed to reducing the surface contact of the guide wire within a catheter lumen or a body lumen, and providing a unique tactile feedback to the clinician or physician thus improving his or her control and awareness of wire movement. The present invention further diminishes the potential for generating particulate in the lubricious hydrophilic coating during motion of the guide wire in a catheter, because of the reduced contact between the catheter lumen and the guide wire surface. Lastly, the present invention provides a guide wire surface that minimizes the phenomenon of "watermelon seeding," which describes the inadvertent shifting of the guide wire relative to the lesion when the two structures catch and then overslip due to the low friction of the guide wire coating.

In one embodiment, the present invention contemplates an intraluminal guide wire comprising an elongated core having a proximal core section and a distal core section having a distal end, wherein at least a section of the elongated core includes at least one of randomized or non-randomized tactile surface contours. The guide wire preferably includes an uninterrupted polymer coating made of generally uniform thickness adhering to at least a portion of the elongated core and having a surface contour that follows the at least one of randomized and non-randomized tactile surface contours in the elongated core. Thus, in this embodiment, the randomized or non-randomized tactile surface contour in the elongated core and elsewhere is translated into a like contour at the polymer coating surface. In other words, bumps in the surface of the wire core translate to bumps in the surface contour or texture of the polymer coating. Preferably, the coating has a generally uniform thickness over the surface contours as well as the flat areas of the wire core.

In another embodiment of the present invention, a guide wire comprises an elongated core having a proximal core section and a distal core section including a taper transitioning to a distal end wherein an exterior surface of the distal core section is relatively smooth. In one variation, a polymer coating of uniform thickness adheres to at least a portion of the distal core section and follows the profile of the taper. In another variation, the outside diameter (O.D.) of the polymer coating does not follow the tapered profile although the inside diameter (I.D.) does follow the taper. This results in a constant O.D. for the guide wire even at the taper and the coating has a variable thickness. In either variation, the polymer coating has at least one of randomized or non-randomized tactile surface contours.

The surface contours in this embodiment are generated in the surface of the polymer coating only and do not originate from the surface texture of the underlying wire core. With the polymer coating that has a generally uniform thickness along the length of the guide wire, the specific coating section with its surface irregularity creating the surface contour or texture is still loosely described as having a uniform thickness. And the uniform thickness polymer coating follows the profile of the core such as in a tapered or step down transition.

In various embodiments of the present invention, the surface contour can include a bump, a divot, a helical groove pattern, a rib, an undulation, a longitudinal groove, ridges and dips, a circumferential groove, or the like. As mentioned above, these tactile surface contours may be generated in the surface of the polymer coating only or may originate in the surface of the wire core which then is translated into the outer surface of the polymer coating.

The present invention further contemplates a method for providing an intraluminal guide wire comprising the steps of providing an elongated core having a proximal core section and a distal core section having a smooth exterior surface. The method further includes tapering the profile of the elongated core to transition into a distal end, and heating and extruding a polymer through a die to adhere to at least a portion of the elongated core to create a polymer coating of generally uniform or variable thickness, and imparting into the polymer coating at least one of randomized and non-randomized tactile surface contours.

In various alternative embodiments, the present invention includes localized heating of the polymer coating to create the surface texture. The localized heating may originate from a laser or a heat source that is brought into proximity of the polymer coating in cycles or randomly at various predetermined feed rates over the wire core. Moreover, the surface contours or texture in the wire core or even the polymer coating can be generated by sand, shot, or particle blasting the wire core or by drawing through a die to create a ridge, for example. These and other advantages of the invention will become more apparent from the following detailed description when taken in conjunction with the accompanying exemplary drawings.

BRIEF DESCRIPTION OF THE DRAWINGS

FIG. 1 is a side elevational view partially in section of one embodiment of the present invention guide wire.

FIG. 2 is a cross-sectional view taken along line 2-2 in FIG. 1 showing a coating over the wire core.

FIG. 3 is a cross-sectional view taken along line 3-3 of FIG. 1.

FIG. 4 is a partial side elevational view of an alternative embodiment guide wire.

DETAILED DESCRIPTION OF THE PREFERRED EMBODIMENTS

Figures 5, 6, 7, 8, 9, 10, 11, 12:
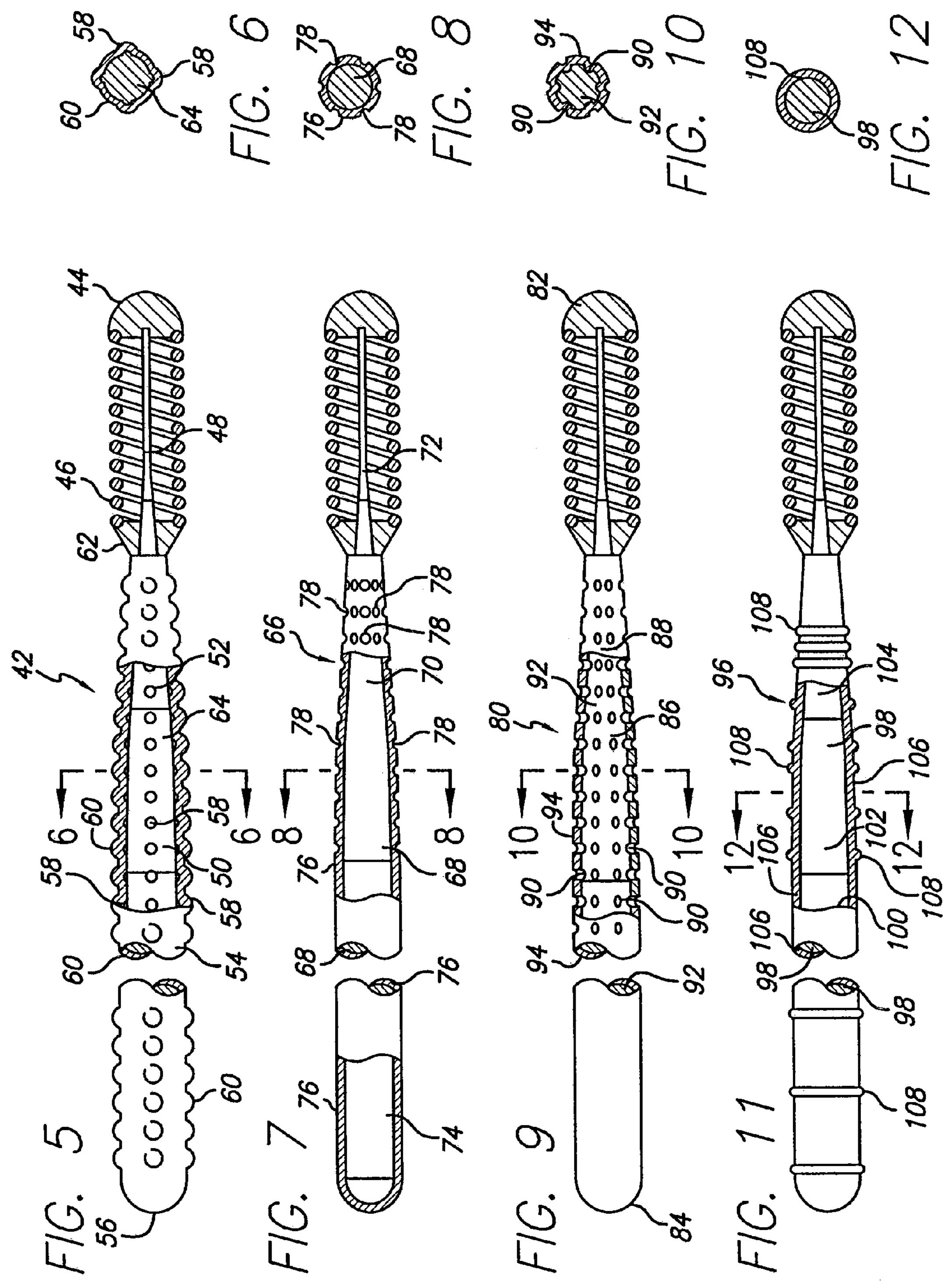
FIG. 5 is a side elevational view partially in section showing a guide wire having bumps and conforming contours in the coating thereon.
FIG. 6 is a cross-sectional view of the guide wire taken along line 6-6 of FIG. 5.
FIG. 7 is a side elevational view of a guide wire partially in section having a smooth core surface and divots in the coating thereon.
FIG. 8 is a cross-sectional view taken along line 8-8 in FIG. 7.
FIG. 9 is a side elevational view of a guide wire partially in section showing pits or divots in the core surface and a conforming surface texture in the coating thereon.
FIG. 10 is a cross-sectional view taken along line 10-10 of FIG. 9.
FIG. 11 is a side elevational view of a guide wire partially in section showing a smooth surface on the wire core with ridges formed in the coating.
FIG. 12 is a cross-sectional view taken along line 12-12 of FIG. 11.

The present invention is directed to an elongated intracorporeal device such as a guide wire having a surface texture. The surface texture depending on location is helpful for minimizing friction between the guide wire and the catheter lumen or body lumen, and provides tactile feedback to the physician if located at the proximal end. In various embodiments, the tactile and friction-reducing surface texture in the guide wire coating is created from texturing the guide wire core underneath which is translated to the coating surface. Alternatively, the texturing is created solely in the surface of the coating that overlies a smooth surface of the wire core.

FIG. 1 is a side elevational view partially in section of one embodiment of the present invention guide wire 10. The guide wire 10 includes an elongated core having a proximal core section 12 and a distal core section 14. In this embodiment, the entire wire core is made from a single material such as stainless steel. In various alternative embodiments (not shown), the proximal core section can be made from a high strength steel while the distal core section 14 is made from a superelastic alloy such as nickel-titanium or the like. The two core sections can be joined by a weld or adhesive, and/or by an interconnecting hypotube made from various materials.

Returning to FIG. 1, the guide wire 10 includes optional tapered sections 16, 18. Specifically, the present invention contemplates one or more tapered profiles at varying degrees of taper, although straight, curved, and/or stepped profiles are also contemplated. The guide wire 10 further includes a coating 20 disposed on and adhering to the wire core 22. The surface coating 20 or the surface of the wire core 22, or both, include surface textures as illustrated in FIGS. 5-16. For simplicity in illustration, the surface textures are not shown in FIGS. 1-4.

The surface coating 20 may only partially cover the guide wire core 22 or may envelope the entire core altogether. Toward the distal end 24 of the guide wire 10 is a flexible member 26. Preferably the flexible member 26 is one or more helical coils welded, bonded, soldered, or otherwise attached to the distal core section 14. In the embodiment shown, the flexible member 26 is attached at its proximal end by a weld or solder mass 28 and at its distal end by a solder ball 30 or similar rounded tip. Furthermore, the guide wire 10 features a flattened distal tip 32 that extends into the solder ball 30. FIGS. 2 and 3 are cross-sectional views of the guide wire 10 taken along lines 2-2 and 3-3 of FIG. 1, respectively.

FIG. 4 is a partial side elevational view of the distal core section 34 of an alternative embodiment guide wire that has a separate shaping ribbon 36 extending from the distal extremity of the wire core 38 or, as shown, from the weld mass 40. The guide wire in FIG. 4 has optional tapered sections 16, 18 as seen in FIG. 1 and an optional solder ball 30. The FIG. 4 embodiment also has a flexible member 26. The coating 22 shown in FIGS. 1 and 2 may extend beneath the flexible member 26 or terminate at any point along the length of the wire core.

FIGS. 5-16 depict various embodiments creating a textured surface in the guide wire according to the present invention. In these drawings, the surface textures have been exaggerated in their relative size to better illustrate their unique features, and accordingly, the drawings are not to scale.

FIG. 5 is a side elevational view of a guide wire 42 similar in construction to that shown in FIG. 1. The guide wire at the distal end 44 includes one or more flexible members 46 surrounding a flattened distal end 48.

The guide wire 42 of FIG. 5 includes optional tapered sections 50, 52 transitioning distally to a flattened distal end 48. Moving proximally, the tapered section 50 transitions into a straight proximal core section 54 terminating at the proximal end 56. As best illustrated in the partially cross-sectioned area in FIG. 5, the wire core 64 of the guide wire 42 includes bumps 58 disposed along the surface thereof. These bumps 58 may be in an organized, non-randomized pattern with uniform shapes and sizes; or they may be randomized in their locations, sizes and shapes.

Indeed, the bumps 58 have sufficient amplitude or height to change the surface contour, but the generally straight or tapered profile of the wire core remains unchanged. In other words, the bumps 58 change the surface texture of the wire core, but do not change and are independent of the overall profile of the wire core, be it straight, tapered, stepped, curved, or any combination thereof.

Overlying the wire core 64 is a coating 60 that in this embodiment preferably extends from the proximal end 56 to a weld mass 62. Importantly, the coating 60 follows or conforms to the surface texture delineated by the bumps 58 as well as the overall profile delineated by the straight, curved, or tapered profiles of the wire core 64. In other words, as the outside diameter of the wire core 68 changes, so does the outside diameter of the coating 60 such that the coating thickness is relatively constant along the length of the wire core 64.

FIG. 6 is a cross-sectional view of the guide wire 42 taken along line 6-6 of FIG. 5. This cross-sectional view shows the wire core 64 having bumps 58 disposed in a regular pattern at 90 degrees apart around its circumference. FIG. 6 further shows the coating 60 with a relatively uniform thickness around the circumference and having bumps in its surface conforming to the bumpy surface texture of the underlying wire core 64.

In the embodiment shown in FIG. 5, the bump 58 pattern in the wire core 64 extends almost the entire length of the wire core 64. Naturally, the bump pattern may cover only a portion thereof, and the bumps 58 may be interspersed in patterns other than that shown in FIG. 5. Also, the wall thickness of the coating 60 is generally uniform, but in alternative embodiments may be thicker or thinner at those locations overlying the bumps 58.

The bumps 58 in the wire core 64 can be created by liquid metal sputtering or like metallization techniques, or from solder, braze, weld, adhesive beads deposited onto the surface of the wire core 64. The coating 60 is then built up on the bumpy substrate thus creating the bumpy textured surface shown in FIG. 5.

FIG. 7 is a side elevational view partially in section of an alternative embodiment guide wire 66. In this embodiment, the wire core 68 has a single tapered section 70 transitioning into a flattened distal end 72 in the distal-direction, while transitioning to a straight proximal core section 74 in the proximal direction. The overall profile of the wire core 68 includes the straight proximal core section 74 and the tapered section 70.

The surface of the wire core 68 is relatively smooth without any surface texture or contour. However, a coating 76 deposited on the smooth surface wire core 68 itself has surface textures in the form of spaced apart divots 78. As seen in the partial sectional view of FIG. 7, the coating 76 generally follows the straight profile or tapered profile of the wire core 68, with a thickness of the coating that is generally uniform except at the divots 78 where the thickness is diminished by the depth of the divots 78. In various alternative embodiments, the depths of the divots may range from just a slight indentation in the coating surface to a through hole exposing the wire core surface. In this embodiment, the surface texturing by way of the divots 78 is concentrated at the tapered section 70 while the proximal core section 74 has no surface texturing in the coating or in the surface of the wire core 68.

FIG. 8 is a cross-sectional view of the wire core 68 taken along line 8-8 of FIG. 7. As seen in this view, the divots 78 are preferably spaced around the circumference of the wire core 68 in approximately 45 degree increments. These types of divot patterns in the coating 76 can be generated by, for example, laser drilling, molding, casting, local application of heat, or the like.

FIG. 9 is a side elevational view, partially in section, of another alternative embodiment guide wire 80. This guide wire 80 features a distal end 82 and a proximal end 84 with tapered sections 86, 88 therebetween. The tapered sections 86, 88 proximate to the distal end 82 have divots 90 that are spread along the surface of the wire core 92. Similar to the embodiment in FIG. 5, these surface impressions or depressions on the wire core 92 are translated into the surface texture of the overlying coating 94. Also, the coating 94 generally follows the straight, curved, stepped, or tapered profile of the wire core 92 while maintaining a generally uniform thickness along the length thereof. At the divots 90, the indentation of the substrate is duplicated in an overlying indentation or divot in the coating surface. Accordingly, the divots 90 in the wire core surface are generally duplicated in the surface of the coating 94.

FIG. 10 is a cross-sectional view of the guide wire 80 taken along line 10-10 of FIG. 9. The cross-sectional view shows the divots 90 dispersed 360 degrees around the circumference of the wire core surface and likewise the indentations are translated to the surface of the coating 94 that surrounds the wire core.

The pattern of indentations, pits, or divots 90 shown in FIG. 9 can be created by, for example, laser cutting, EDM, mechanical rolling with a patterned die, stamping, or the like. The pattern of divots 90 may be uniform as shown in FIG. 9, or may be a randomized pattern with varying divot sizes. Further, the pattern of divots or similar surface texturing may be concentrated at a specific portion of the guide wire or along the entire length thereof. The depth of the divots 90 can be controlled by the energy applied during the laser cutting or EDM processes, by the size of the relief pattern in the rolling die and the pressure applied by it to the surface of the wire core, by bead blast intensity and velocity, or the like.

FIG. 11 is a side elevational view of another alternative embodiment guide wire 96. In this embodiment, the partial cross-sectional view shows a smooth surface wire core 98 with a straight 100, tapered 102, 104, or curved (not shown) profile. A coating 106 in the FIG. 11 embodiment covers those straight and tapered profile sections. The coating 106 has a generally uniform thickness along these sections and conforms to the straight or tapered profile. Furthermore, the coating 106 has ridges 108 randomly positioned along the length of the wire core 98. The ridges 108 rise above the surface of the coating 106 and span the circumference of the wire core 98. As such, the coating 106 has a generally uniform wall thickness except at the ridges 108 where the wall thickness increases slightly.

FIG. 12 is a cross-sectional view taken along line 12-12 of FIG. 11 showing the generally untextured outer surface of the wire core 98 and a ridge 108 just proximal to the section cut line. Therefore, in this embodiment, the ridges 108 formed into the surface of the coating 106 form the textured or contoured surface.

Figure 17:
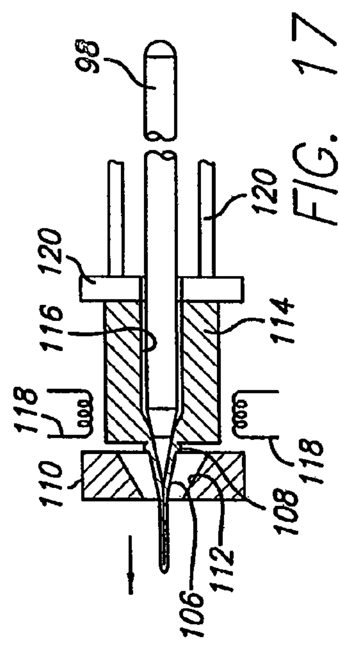
FIG. 17 is a schematic view of a coating process in which the polymer and wire core are extruded through a die.

FIG. 17 shows one preferred process for creating a coating with surface texturing; the surface texturing here are ridges 108. In FIG. 17, guide wire core 98 is fed through a die 110 having a tapered orifice 112. The wire core 98 again has straight and tapered profiles. A solid polymer cartridge 114 surrounds the wire core 98 as it passes through a lumen 116 therein. Proximate to the die 110 is a heat source 118 used to melt the polymer nearest the die 110. A plunger 120 also applies pressure on the cartridge 114 forcing melted polymer into the orifice 112 as the wire core 98 passes therethrough. Accordingly, the wire core 98 is fed in the direction of the arrow shown in FIG. 17 while the polymer cartridge 114 is simultaneously melted by the heat source 118 and force fed into the orifice 112 under plunger pressure 120.

If this process proceeds without disturbance, a generally uniform and concentric coating is adhered to the surface of the wire core. However, if the feed speed through the die 110 is changed, or the feed is stopped, for example, a ridge 108 is formed as shown in FIG. 17. More background details of the process are described in U.S. Pat. No. 6,419,745 (Burkett et al.), titled "Method and Apparatus for Polymer Application to Intracorporeal Devices," whose entire contents are hereby incorporated by reference.

Other parameters that can be adjusted to build the ridges 108 in FIG. 17 include heating the polymer cartridge 114 to a higher temperature with a greater fluid flow rate while slowing the feed rate of the wire core 98. This results in a greater deposit or thickness in the coating 106 as compared to the other portions of the coating 106. Also, resuming to normal feed speed after a speed change or interruption changes the thickness of the coating 106 deposited on the substrate. Furthermore, the height of the ridges 108 above the surface of the coating 106 can be adjusted by changes in the relative feed speed and/or by adjusting the flow rate of the melted polymer as controlled by plunger pressure and heat source temperature. Indeed, in one embodiment, the raised ridges 108 can be created by momentarily increasing the plunger pressure against the cartridge 114 thus momentarily depositing an extra amount of melted polymer on the substrate. This occurs while all of the other processing parameters remain constant. Through the aforementioned processes, the ridges 108 can be spaced apart uniformly or randomly spaced.

FIGS. 13-16 show various alternative embodiment surface textures. It is acknowledged that these drawings show the coatings on a tapered portion of the wire core, but it is understood that the textured surfaces can be generated at any part of the wire core along its length. Again, the relative size of the texturing has been exaggerated for the sake of illustration.

Figure 18:
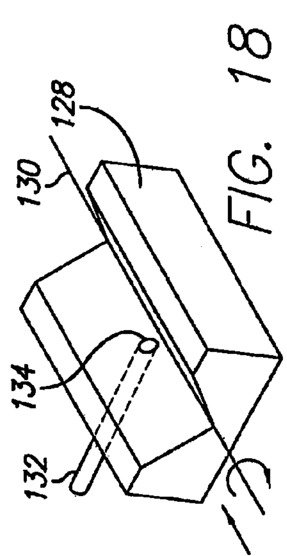
FIG. 18 is a perspective view of a V-block fixture used to hold a wire core for laser cutting a surface texture therein.
Figure 13:
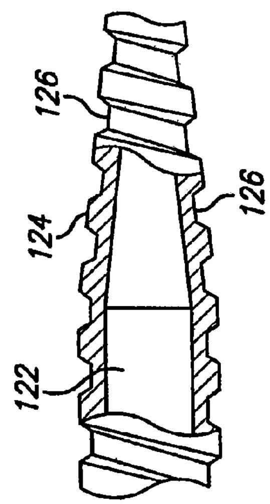
FIG. 13 is a partial side elevational view of a distal core section of a wire core with a partial cross-section showing a helical surface contour in the coating.

FIG. 13 shows a partial side elevational view of a wire core 122 having a coating 124 that features circumferential grooves 126 that are preferably formed into a helical pattern. This pattern can be generated in the surface of the coating 124 through a fixture shown in FIG. 18. A V-block 128 has a V-shaped groove or notch that receives the length of a wire core 130. Situated preferably perpendicular to the longitudinal axis of the wire core 130 is a laser 132 with a lens aperture 134 immediately adjacent to the wire core 130 at or near the vertex of the notch of the V-block 128. As the wire core 130 is fed lengthwise as indicated by the arrow, the wire core 130 is rotated in a clockwise or counterclockwise direction. The laser 132 is energized and cuts a pattern in the coating that resembles the helically grooved 126 surface texture shown in FIG. 13. Naturally, the intensity of the laser and the feed and rotational speed of the wire core 130 through the V-block 128 affect the final surface configuration and depth of the grooves 126.

Figure 14:
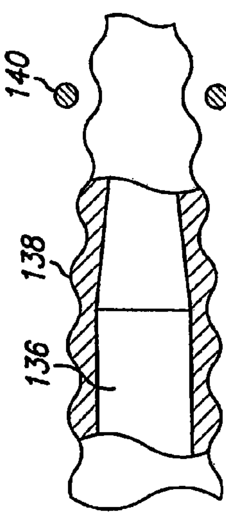
FIG. 14 is a partial side elevational view, partially in cross-section, showing an undulating surface contour.

FIG. 14 is a partial side elevational view of a wire core 136 with a coating 138. An initial uniform thickness coating over the wire core 136 can be achieved by the process disclosed in connection with FIG. 17 and U.S. Pat. No. 6,419,745 (Burkett et al.). The application of heat to create the surface undulations would thus be a subsequent step. In this embodiment, the coating 138 has an undulating surface texture created by moving a heat source 140 close to and then away from the coating 138. This action melts portions of the coating 138 while not affecting other portions thus generating the wavy surface texture. The heat source 140 can be in the form of a hot mold that closes down on the wire to form the surface wave pattern. Another option involves a fixture that would place the wire core 136 inside a series of heated coils. Heating coils close to the coating 138 cause the polymer to flow away from the heat source again creating the wavy surface texture.

Figure 15:
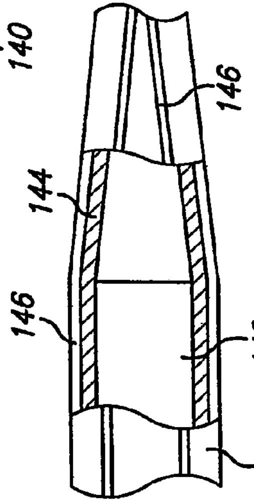
FIG. 15 is a partial side elevational view, partially in cross-section, showing longitudinal grooves in the surface contour.

FIG. 15 is a partial side elevational view of a wire core 142 having a coating 144 that features longitudinal or lengthwise grooves 146 creating the surface texture. The longitudinal grooves 146 preferably do not extend deeply into the coating 144 to prevent segmenting the coating into discrete pieces. Such longitudinal grooves 146 can be laser cut into the coating 144 through a process such as that shown in FIG. 18 using a V-block 128.

Figure 16:
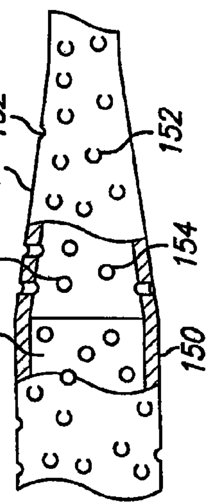
FIG. 16 is a partial side elevational view, partially in cross-section, showing randomized pits or divots in the wire core surface and conforming surface contours in the coating thereon.

FIG. 16 is a partial side elevational view of a wire core 148 with a coating 150 having random divots 152 formed therein. The divots 152 in the coating originate from divots 154 or pits formed into the surface of the wire core 148. These divots 154 are preferably created by shot, bead, sand or particle blasting the surface of the wire core 148 thus generating the randomly pitted or scarred surface texture. The surface texture of the wire core 148 translates to corresponding pitting or divots 152 in the surface coating 150.

Figure 19:
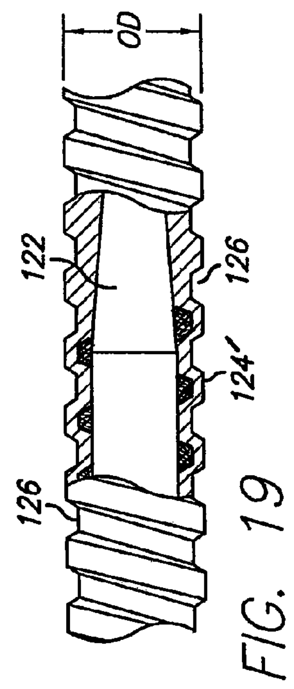
FIG. 19 is a partial side elevational view of a distal core section of a wire core with a partial cross-section showing a helical surface contour in the variable thickness coating, and showing the coating having a constant outside diameter (O.D.).

FIG. 19 shows an embodiment very similar to that shown in FIG. 13 in a partial side elevational view of a wire core 122 having a coating 124' that features circumferential helical grooves 126. In this embodiment, however, the outside diameter (O.D.) of the polymer coating 124' is constant along the length of the core while the inside diameter (I.D.) follows and adheres to the overall profile of the wire core 122, here a taper. Therefore, in this embodiment, the thickness of the polymer coating 124' varies along the length of the core 122 and is not uniform. The variable thickness coating 124' can be adapted to any of the foregoing embodiments shown in FIGS. 5-16.

The present invention coating as mentioned in the above embodiments is preferably a polyurethane polymer, although any polymer that meets design requirements can be used. The spacing between surface textures or contour interruptions range between about 0.1 cm to 0.3 cm along the length of the wire core. In one embodiment, the textured polymer coating is located on the distal working section of the wire core, which is typically between 25 to 45 cm from the distal tip of the wire core and more preferably the distal 45 cm, although the polymer coating may be terminated at the distal tip coils as shown in FIG. 5, 7, 9, or 11, for example. In another preferred embodiment, the amplitude or height above the main polymer coating surface of the surface texture interruption would be from 0.0002 to 0.002 inch, with the preferred embodiment having an amplitude between 0.0005 and 0.001 inch. Reasonable spacing between surface texture interruptions would be preferably between 0.1 to 0.2 cm and could range from 0.05 to 2 cm.

In various alternative embodiments, the surface coating can be made from a fluoropolymer or fluoropolymer resin materials. The surface could then be randomly or non-randomly textured, resurfaced, or scarred using a laser, UV light, radiation, or other forms of heat and energy transmission. As mentioned earlier, the texturing of the surface of the wire core can be any mechanical means such as textured rollers, scraping, dimpling, impingement, sand blasting using aluminum oxide, carbide, sodium bicarbonate powders, stamping, pad printing, etc.

The fluoropolymer coating may be co-extruded onto the wire core through the process described in connection with FIG. 17. Such a fluoropolymer may be PTFE or any type of fluoropolymer based material, blended fluoropolymer with other non-fluoropolymers, primed, layered, impinged, baked, chemically adhered on one or more layers with any/either PTFE, FEP, TEFLON 1 coats, PTFE/PFA blends, PFA, ETFE, DuPont TEFLON coatings, Xylan coatings, DuPont TEFLON S coating, DuPont TEFLON P coating, Akzo Nobel & Acheson colloids, or other like fluoropolymers. Although not shown, the textures imparted or formed into the surface of the coating can include various shapes such as round, oblong, square, rectangle, triangular, polygonal, teardrop, and other geometric shapes.

Although not shown, the present invention contemplates more than one coating being applied to the wire core. Therefore, the embodiments shown in the drawing figures may have multiple coatings yet still reflect the surface textures depicted.

The wire core 22 may have an optional lubricious coating such as a fluoropolymer, e.g., TEFLON available from DuPont, that extends the length of the wire core or a portion thereof. The distal core sections 14, 34, may optionally be covered with a lubricious coating such as that used by Advanced Cardiovascular Systems, Inc. under the commercial name MICROGLIDE. Hydrophilic coatings may also be employed to cover the wire core partially or entirely.

The guide wires of the present invention may have typical guide wire dimensions. Guide wire length may generally be about 90 to about 300 cm, and for use within a patient's coronary anatomy commercially available guide wires are typically about 175 cm in length. Longer and longer guide wires, e.g., up to 190 cm in length, are being offered commercially by a variety of suppliers. The proximal core section 12 may have a length of about 65 to about 280 cm, preferably about 150 to about 200 cm and a diameter generally about 0.008 to about 0.035 inch (0.20-0.89 mm), typically about 0.010 to about 0.020 inch (0.25-0.51 mm) for coronary artery uses. The distal core section is preferably much shorter than the proximal core section and generally is about 6 to about 40 cm, preferably about 8 to about 30 cm in length and tapers in the distal direction in one or more steps to smaller cross-sectional dimensions.

The tapered portion of the distal core section is preferably followed distally with a manually shapable flattened core segment or shaping ribbon of about 1 to 4 cm in length which preferably has essentially constant transverse dimensions, e.g., 0.0005-0.002 inch (0.013-0.051 mm) by 0.002-0.006 inch (0.051-0.152 mm), typically about 0.001 by 0.003 inch (0.025-0.076 mm). A helical coil having transverse outer dimensions about the same as or slightly less than the proximal core section is secured by its distal end to the flattened distal tip of the core member, e.g., by means of solder, and by its proximal end at an intermediate position on the tapered distal core section so that the distal end of the tapered core section resides within the interior of the coil. The helical coil 14 may be formed all or in part of stainless steel, a suitable radiopaque material such as platinum or alloys thereof or other material such as stainless steel coated with a radiopaque material such as gold. The wire from which the coil is made generally has a transverse diameter of about 0.0015 to about 0.003 inch (0.04-0.08 mm) for coronary applications and up to 0.07 inch (0.18 mm) for peripheral applications. The overall length of the coil 14 is about 2 to about 15 cm, preferably about 2 to about 6 cm. Multiple turns of the coil 14 may be expanded to provide additional flexibility.

Unless otherwise described herein, conventional materials and manufacturing methods may be used to make the guiding members of the present invention. Additionally, various modifications may be made to the present invention without departing from the scope thereof. Although individual features of embodiments of the invention may be shown in some of the drawings and not in others, those skilled in the art will recognize that individual features of one embodiment of the invention can be combined with any or all of the features of another embodiment.

What is claimed:

1. An intraluminal guide wire, comprising:

an elongated core having a proximal core section and a distal core section including a taper transitioning to a distal end;

wherein an exterior surface of the distal core section includes randomized tactile surface contours as part of the distal core section itself;

a polymer coating of generally non-uniform thickness adhering without a gap to at least a portion of the distal core section including at least a portion of the tapered transition with a coating profile not following a tapered profile of the elongated core, the polymer coating having tactile surface contours following the randomized surface contours of the exterior surface of the distal core section; and a flexible tubular member disposed over the distal core section.

2. The intraluminal guide wire of claim 1, wherein the tactile surface contours includes a rib.

3. The intraluminal guide wire of claim 1, wherein the tactile surface contours includes a helical pattern.

4. The intraluminal guide wire of claim 1, wherein the tactile surface contours includes a longitudinal groove.

5. An intraluminal guide wire, comprising:

an elongated wire core having a proximal wire core section and a distal wire core section including a taper transitioning to a distal end;

wherein an exterior surface of the distal wire core section includes randomized tactile surface contours that are part of the distal wire core section itself;

a polymer coating of generally non-uniform thickness adhering to and contiguous with at least a portion of the distal core section including at least a portion of the tapered transition with a coating profile not following a tapered profile of the elongated core, the polymer coating having tactile surface contours following the randomized surface contours of the exterior surface of the distal core section;

a flexible tubular member disposed over the distal core section, wherein:

the surface contours have a surface-to-peak amplitude of about 0.0002 to 0.0020 inch;

the flexible tubular member is disposed over the polymer coating;

the proximal core section includes a high strength steel and the distal core section includes a nickel-titanium alloy; and the polymer coating includes a fluoropolymer.

* * * * *